United States Patent [19]

Hargis

[11] 4,261,864
[45] Apr. 14, 1981

[54] PROCESS FOR THE SELECTIVE PREPARATION OF ALPHA-OLEFIN FROM SYNTHESIS GAS

[75] Inventor: Duane C. Hargis, Pleasant Ridge, Mich.

[73] Assignee: Ethyl Corporation, Richmond, Va.

[21] Appl. No.: 95,414

[22] Filed: Nov. 19, 1979

[51] Int. Cl.$^3$ .................. B01J 23/78; B01J 23/84
[52] U.S. Cl. ............................................... 252/470
[58] Field of Search ..................... 252/470; 423/606

[56] References Cited

U.S. PATENT DOCUMENTS

| 2,729,664 | 1/1956 | Kirshenbaum | 252/474 X |
| 2,731,486 | 1/1956 | Rottig | 252/474 X |

Primary Examiner—W. J. Shine
Attorney, Agent, or Firm—Donald L. Johnson; Joseph D. Odenweller; Willard G. Montgomery

[57] ABSTRACT

A process for selectively preparing alpha-olefins having from 2 to about 22 carbon atoms by contacting a gaseous mixture containing carbon monoxide and hydrogen with an iron tungstate-alkali metal hydroxide catalyst at reaction conditions correlated so as to favor the formation of a substantial proportion of such alpha-olefin product.

3 Claims, No Drawings

PROCESS FOR THE SELECTIVE PREPARATION OF ALPHA-OLEFIN FROM SYNTHESIS GAS

BACKGROUND OF THE INVENTION

This invention relates to a Fischer-Tropsch reaction. More particularly, this invention relates to the reaction between carbon monoxide and hydrogen in the presence of an iron tungstate catalyst in combination with an alkali metal hydroxide to selectively produce alpha-olefins under reaction conditions correlated to produce such olefin product.

It is well known that valuable organic compounds may be produced by the catalytic hydrogenation, under pressure, of oxides of carbon, particularly carbon monoxide. The prior art is replete with numerous metallic catalysts which have been utilized, both in supported and non-supported forms. Efforts to convert synthesis gas (i.e. carbon monoxide and hydrogen) into a definitive class of products, however, has not been readily accomplished. Most synthesis gas conversion processes generally tend to give a wide spectrum of products, for example, hydrocarbons and oxygenated hydrocarbons having a broad distribution of carbon atom contents. Alpha-olefins, particularly alpha-olefins having from 6 to 12 carbon atoms are particularly useful in the synthetic chemical industry finding uses, for example, as intermediates for alcohol synthesis and as detergents in lube oil and fuel compositions. Heretofore, these olefins have been commercially obtained principally from the polymerization of lower olefins produced by the thermal decomposition of petroleum fractions and natural gas. Accordingly, with the decline of available reserves of natural gas and petroleum crude, it is highly desirable to find alternative means for producing such olefins which are not dependent upon natural gas and petroleum feedstock.

It is therefore an object of the present invention to provide a process for the selective conversion of synthesis gas into alpha-olefin products.

It is another object of the present invention to provide an iron tungstate-alkali metal hydroxide catalyst which is highly reactive and highly selective for converting synthesis gas into alpha-olefin products.

Other objects and advantages of the present invention shall become apparent from the accompanying description and examples.

SUMMARY OF THE INVENTION

The present invention provides a method for selectively producing alpha-olefins having from 2 to about 22 carbon atoms from gaseous mixtures of carbon monoxide and hydrogen using an iron tungstate-alkali metal hydroxide catalyst.

DESCRIPTION OF THE PREFERRED EMBODIMENT

This is achieved by contacting, in a reaction zone, a gaseous mixture of carbon monoxide and hydrogen with a catalyst comprising solid particles of iron tungstate which have been treated with an alkali metal hydroxide at reaction conditions correlated to produce such alpha-olefin product. Thus, a preferred embodiment of the present invention is a process for selectively producing alpha-olefins having from 2 to about 22 carbon atoms which comprises the step of contacting a gaseous mixture containing carbon monoxide and hydrogen with a catalyst comprising iron tungstate and an alkali metal hydroxide at reaction conditions correlated so as to favor the formation of a substantial proportion of such alpha-olefin product.

The catalyst used in the practice of this invention is believed novel and its constituents different from those of the prior art. By use of the catalyst according to this invention, it is possible to carry out the reduction of carbon monoxide to obtain a mixture of alpha-olefins having from 2 to about 22 carbon atoms. The catalyst according to this invention comprises solid particles of iron tungstate which have been treated with an alkali metal hydroxide. Thus, another embodiment of the present invention is a catalyst for converting gaseous mixtures of carbon monoxide and hydrogen to alpha-olefins having from 2 to about 22 carbon atoms said catalyst comprising iron tungstate and an alkali metal hydroxide.

PROCESS DISCUSSION

The reaction is conducted at more or less conventional Fischer-Tropsch reaction conditions of temperature, pressure, gas composition, and space velocity so that conventional technology and equipment may be used. Over all, the reaction is conducted at reactive conditions of temperature, pressure, gas composition and space velocity which are correlated to achieve optimal selectivity for alpha-olefins. The reaction efficiency, or selectivity, to alpha-olefins is invariably at least about 45% and is usually upwards of about 50%. Under preferred conditions it exceeds 50% and can reach approximately 54% excluding carbon dioxide from the product. Selectivity is defined herein as the percentage of carbon atoms converted from carbon monoxide to a specified compound or compounds other than carbon dioxide.

The reaction is highly exothermic with the thermodynamic equilibria and the kinetic reaction rates being governed by the reaction temperature. Average catalyst bed temperatures are usually within the range of about 200° C.–300° C., but for optimum conversions, bed temperatures are kept within the range of about 225° C. to about 300° C., typically about 250° C. to 300° C.

The reaction temperature appears to be an important process variable affecting not only total productivity, but selectivity towards the desired alpha-olefin products. With all other variables held constant, as the reaction temperature increases within the range studied the efficiency of alpha-olefin production also increases. Olefin distribution is also effected by changes in temperature. For example, excluding the lighter olefins i.e. $C_2$–$C_4$, at 250° C., with all other variables held constant, olefin distribution peaks at $C_6$–$C_7$. At 300° C., however, there is a shift in distribution towards the higher molecular weight $C_8$–$C_9$ olefins.

In the above discussion, the indicated temperatures are expressed as average, or mean, reaction bed temperatures. Because of the tendencies to produce increased amounts of higher olefins at higher reaction temperatures, it is desirable for the purposes of the present invention that for optimal selectivity to long chain ($>C_5$ olefin) alpha-olefin production that temperatures be controlled so as to fall within the range of about 275° C. to about 300° C.

The reaction zone pressure is desirably within the range of about 50 psig to about 250 psig. A reaction zone pressure of approximately 225 psig is preferred.

The ratio of hydrogen to carbon monoxide in the synthesis gas may vary somewhat. Normally, the mole ratio of hydrogen to carbon monoxide is within the range of 2:1 to 1:2. Preferably, the mole ratio of hydrogen to carbon monoxide is 1:1.

Conversion is conveniently achieved by employing a high space velocity correlated with other reaction variables (e.g. temperature, pressure, gas composition, catalyst, etc.,). Space velocity of from about 1200 to 2400 gas hourly space velocities (volumes of reactant gas at 0° C. and 760 mm mercury pressure, per volume of catalyst per hour) are generally employed. A preferred gas hourly space velocity is approximately 1200 GHSV.

A highly preferred embodiment of the present invention is a process for producing alpha-olefins having from 2 to about 22 carbon atoms comprising contacting a gaseous mixture of carbon monoxide and hydrogen with a catalyst comprising iron tungstate and an alkali metal hydroxide at reaction conditions correlated to produce such alpha-olefin product, said reaction conditions including a temperature within the range of from about 200° C. to about 300° C., a pressure within the range of about 50-250 psig, and a mole ratio of hydrogen to carbon monoxide of 1:1.

THE CATALYST

The catalyst of iron tungstate and alkali metal hydroxide is provided in the reaction zone as particles, such as placing particles of iron tungstate which have been treated with an alkali metal hydroxide in the reaction zone, generally supported by an inert porous packing material, such as, for example, glass wool. Another way is to deposit the catalyst particles in a basket-like container in the reaction zone. The catalysts of the present invention are all prepared by essentially the same sequence of steps. An aqueous solution of an alkali metal hydroxide is added to a beaker containing particles of iron tungstate. Potassium hydroxide has been found to be a particularly effective alkali metal hydroxide for use in the practice of the present invention. The fact that potassium hydroxide has proven to be effective would appear to indicate that other alkali and/or alkaline earth metal hydroxides may also be used in the practice of the present invention. Generally, from about 0.1 weight percent to about 3.0 weight percent of alkali metal hydroxide based on the total weight of the catalyst composition is preferred. Especially preferred is an iron tungstate-alkali metal hydroxide catalyst composition containing about 1.0 weight percent of the alkali metal hydroxide. In preparing the catalyst composition of the present invention, the amount of alkali metal hydroxide solution added to the iron tungstate particles is an amount sufficient only to completely wet the iron tungstate particles and no more. Typically, 5 ml of a solution of alkali metal hydroxide in distilled water is used. This technique of catalyst preparation is well known and is commonly referred to as the incipient wetness technique. By contacting the solid particles of iron tungstate with just enough alkali metal hydroxide solution to merely wet the iron tungstate particles with little or no excess solution being used insures that the desired concentration of alkali metal hydroxide will be incorporated into the catalyst composition. After treating the particles of iron tungstate with the alkali metal hydroxide solution, the catalyst material is subjected to drying conditions to lower the water content of the resultant catalyst composition to the lowest possible level. In a typical drying procedure, the catalyst composition is slowly heated from room temperature up to a temperature of approximately 100° C. and is maintained at this temperature for a period of time of at least one hour until substantially all of the water content of the catalyst composition is removed.

As a further required step in the procedure for catalyst production, the dry-state catalyst composition is reduced with hydrogen. It has been found advantageous to conduct the reduction of the catalyst composition by contacting the catalyst composition in a reduction zone with hydrogen, and then heating the catalyst reduction zone slowly from room temperature up to approximately 300° C. It is highly preferred that the catalyst reduction zone be maintained at this temperature for approximately 18 to 24 hours in order to effect reduction of the catalyst composition. For the purposes of the present invention, it appears that complete reduction of iron to the zero valent state is not desirable for optimal production of long chain alpha-olefins.

TEST REACTOR

The reactor used in the practice of the present invention is a stainless steel tube of 0.305 in. internal diameter, 0.375 in. outside wall diameter with a wall thickness of 0.035 in. The length is 14 inches and the reactor capacity is approximately 16.5 ml. The tube is packed with a catalyst prepared as described above deposited on a glass wool support. Carbon monoxide and hydrogen are fed to the reactor in the desired mole ratio from 1750 psig headers. Typically, 5 ml of catalyst are placed in the reactor on the support. The reactor is then pressurized with hydrogen and the flow of carbon monoxide and hydrogen are adjusted to achieve the desired composition. During pressurization of the reactor, the reactor temperature and pressure are adjusted to reaction conditions. At least 5 to 6 hours are allowed for the reactor to come to a steady state before beginning to measure actual time of reaction. The reaction is then allowed to proceed for approximately 24 hours during which a sample of liquid product is collected by cooling the product containing gas through a cold water condenser at approximately 225 psig and then trapping the liquid product in a dry ice-acetone trap having a capacity of approximately 55 cc. The liquid product from the trap and the condenser are then combined to obtain a single liquid sample which is then analyzed by gas chromatography. The non-condensable gases are metered through a wet-test meter to determine the volume of gas, and a gas sample is collected to determine its composition.

The following examples serve to provide specific illustrations of the present invention.

EXAMPLE 1

This example illustrates the preparation of the iron tungstate alkali metal hydroxide catalyst of the present invention.

13.45 grams of iron tungstate particles (200 mesh), obtained commercially from Cerac, Inc., 407 North 13th Street, Milwaukee, Wisconsin, were deposited in a 50 ml beaker. Next, 0.1345 grams of potassium hydroxide dissolved in an amount of distilled water (typically 5 ml) were added to the iron tungstate particles in the beaker. This produced a catalyst composition containing 1.0 weight percent potassium hydroxide. The composition was then heated slowly from room temperature to a temperature of about 100° C. and dried at this temperature for approximately one hour to remove substantially all of the water from the composition. The dried catalyst composition was then placed in the reactor, aforedescribed, on an inert packing support and reduced with hydrogen. This was accomplished by slowly heating the catalyst from room temperature to a temperature of approximately 300° C. while flowing 50 ml per hour of hydrogen over the catalyst. Contact of the catalyst with hydrogen was continued at these conditions for approximately 18 hours.

EXAMPLE 2

This example compares the effect of alkali metal hydroxide loading on the selectivity of the iron tungstate-alkali metal hydroxide catalyst for alpha-olefin products.

13.45 grams of untreated iron tungstate particles (200 mesh) were deposited in the reactor apparatus described in the TEST REACTOR section. The sample was then reduced in hydrogen at 300° C. for approximately 18 hours. Reaction conditions are summarized below.
Temperature; 250° C.
Pressure; 225 psig
Volume Hourly Space Velocity; 1200 hr.$^{-1}$
$H_2/CO$ Molar Ratio; 1:1

The carbon monoxide conversion was found after several hours on stream to be approximately 10 mole percent. The carbon monoxide conversion is defined as 100 times the moles of carbon monoxide converted divided by the moles of carbon monoxide in the feedstock. The reaction product excluding $CO_2$ consisted of:

| Distribution, C % | |
|---|---|
| $CH_4$ | 13.3 |
| $C_2$-$C_4$ paraffinic | 8.5 |
| $C_5$-$C_{22}$ paraffinic | 24.9 |
| $C_2$-$C_4$ olefin | 18.2 |
| $C_5$-$C_{22}$ olefin | 12.5 |
| $C_5$-$C_{22}$ alcohol | 5.4 |
| Other Hydrocarbons | 10.9 |
| Aqueous Oxygenates | 6.2 |

For comparison, an iron tungstate-potassium hydroxide catalyst composition containing 1.0 weight percent potassium hydroxide prepared as described in Example 1 was deposited in the reactor and reduced in hydrogen at 300° C. for approximately 18 hours in the same manner as the untreated iron tungstate catalyst described above. A synthesis gas conversion run using the iron tungstate-potassium hydroxide catalyst was then carried out under the same reaction conditions used in the aforedescribed run for the untreated iron tungstate catalyst. Analysis of the reaction product showed the following:

| Distribution, C % | |
|---|---|
| $CH_4$ | 16.5 |
| $C_2$-$C_4$ paraffinic | 2.2 |
| $C_5$-$C_{22}$ paraffinic | 8.9 |
| $C_2$-$C_4$ olefin | 23.7 |
| $N_5$-$C_{22}$ olefin | 22.6 |
| $C_5$-$C_{22}$ alcohol | 6.4 |
| Other Hydrocarbons | 12.8 |
| Aqueous Oxygenates | 6.7 |

As shown by the foregoing data, the Fischer-Tropsch type product produced by the untreated iron tungstate catalyst was comprised of about 34% paraffins, and about 31% olefins with $C_5$-$C_{22}$ olefins accounting for only about 12.5% of the organic product. The addition of 1.0 weight percent potassium hydroxide to the iron tungstate, however, significantly altered product selectivity. At the same reaction condition, total olefin production increased to approximately 47% of the organic product, while paraffin production decreased to 11.1% of the organic product. Production of $C_5$-$C_{22}$ olefin increased to 22.6% of the organic product. Thus, excluding $CO_2$ from the product, the addition of 1.0 weight percent of potassium hydroxide to the iron-tungstate catalyst, increased total alpha-olefin production to over 46% of the organic product formed, and $C_5$-$C_{22}$ olefin production to approximately 23% of the organic product.

EXAMPLE 3

A series of runs were made to determine the effect of temperature on the reaction of synthesis gas over an iron tungstate-alkali metal hydroxide catalyst containing 1.0 weight percent potassium hydroxide. Temperature was varied from 250° C. to 300° C.; $H_2/CO$ ratio was held constant at 1.0; pressure was 225 psig; and space velocity was maintained at 1200 hr.$^{-1}$ The catalyst used in these runs was prepared according to the procedure set forth in preceeding Example 1 above. The test reactor and the procedure described in the foregoing TEST REACTOR and PROCESS DISCUSSION sections were used. Reaction conditions and product composition data are summarized as Run Nos. 1-3 in Table 1 below.

TABLE 1

Synthesis Gas Reaction Over $FeWO_4$-1% KOH Catalyst

| Run | | | |
|---|---|---|---|
| $H_2/CO$ | 1.0 | 1.0 | 1.0 |
| GHSV | 1200 | 1200 | 1200 |
| Temp., °C. | 250 | 275 | 300 |
| Pressure, psig | 225 | 225 | 225 |
| CO Conv., % | .41 | 1.7 | 3.0 |
| *Distribution, C % | | | |
| $CH_4$ | 16.5 | 13.1 | 16.9 |
| $C_2$-$C_4$ paraffinic | 2.2 | — | — |
| $C_5$-$C_{22}$ paraffinic | 8.9 | 12.4 | 7.3 |
| $C_2$-$C_4$ olefin | 23.7 | 10.7 | 14.5 |
| $C_5$-$C_{22}$ olefin | 22.6 | 37.9 | 39.4 |
| $C_5$-$C_{22}$ alcohol | 6.4 | 10.2 | 8.9 |
| Other Hydrocarbons | 12.8 | 11.5 | 10.0 |
| Aqueous Oxygenates | 6.7 | 4.3 | 3.1 |

*Excluding $CO_2$

As shown by the data in Table 1 above, within the reaction parameters chosen as temperature increases, the formation of long chain alpha-olefins also tends to increase. At 250° C., $C_5$-$C_{22}$ olefin comprised approximately 23% of the organic product. When the reaction temperature was increased to 300° C. however, $C_5$-$C_{22}$ olefin production increased to approximately 40% of the organic product.

Claims to the invention follow.

I claim:

1. A catalyst composition for converting gaseous mixtures containing carbon monoxide and hydrogen to alpha-olefins having from 2 to about 22 carbon atoms, said catalyst comprising iron tungstate and an alkali metal hydroxide which has been reduced with hydrogen.

2. The composition of claim 1 wherein the amount of alkali metal hydroxide ranges from about 0.1 weight percent to about 3.0 weight percent based on the total weight of the composition.

3. The composition of claim 2 wherein said alkali metal hydroxide is potassium hydroxide.

* * * * *